US008937720B2

(12) United States Patent
Russell

(10) Patent No.: US 8,937,720 B2
(45) Date of Patent: Jan. 20, 2015

(54) FILTER WHEEL SPECTROMETER

(71) Applicant: Koninklijke Philips N.V., Eindhoven (NL)

(72) Inventor: James Torrance Russell, Bellevue, WA (US)

(73) Assignee: Koninklijkle Philips N.V., Eindhoven (NL)

( * ) Notice: Subject to any disclaimer, the term of this patent is extended or adjusted under 35 U.S.C. 154(b) by 0 days.

(21) Appl. No.: 13/916,683

(22) Filed: Jun. 13, 2013

(65) Prior Publication Data

US 2013/0270440 A1  Oct. 17, 2013

Related U.S. Application Data

(62) Division of application No. 13/128,799, filed as application No. PCT/IB2009/054860 on Nov. 2, 2009, now Pat. No. 8,477,311.

(60) Provisional application No. 61/115,757, filed on Nov. 18, 2008.

(51) Int. Cl.
  *G01N 21/25* (2006.01)
  *G01J 3/02* (2006.01)
  *G01J 3/36* (2006.01)
  (Continued)

(52) U.S. Cl.
  CPC ............... *G01N 21/255* (2013.01); *G01J 3/02* (2013.01); *G01J 3/0202* (2013.01); *G01J 3/0235* (2013.01); *G01J 3/36* (2013.01); *G01J 2003/1213* (2013.01); *G01J 2003/1226* (2013.01); *G01N 21/3504* (2013.01); *G01N 2021/317* (2013.01)

USPC ............................ 356/418; 356/417; 356/419

(58) Field of Classification Search
  USPC ........................................................ 356/418
  See application file for complete search history.

(56) References Cited

U.S. PATENT DOCUMENTS 3,796,887 A * 3/1974 Vincent et al. ................ 250/565
3,904,880 A * 9/1975 Benz et al. .................... 250/343
(Continued)

FOREIGN PATENT DOCUMENTS

EP       1632762 A2      3/2006
JP    2005P291726 A     10/2005
(Continued)

OTHER PUBLICATIONS

Solomon, Rodney J. "A Reliable, Accurate CO2 Analyzer for Medical Use" Hewlett-Packard Journal, Sep. 1981, vol. 32, No. 9, pp. 1-31.

*Primary Examiner* — Tarifur Chowdhury
*Assistant Examiner* — Omar Nixon

(57) ABSTRACT

A filter wheel and a spectrometer including the filter wheel are disclosed. The filter wheel has a first support structure on which a first plurality of filters are mounted and a second support structure on which at least one filter is provided. A radiation source generates a radiation beam, and a beam splitter splits the radiation beam into a first detection path and a second detection path. The first plurality of filters are selectively movable into the first detection path. The at least one filter on the second support structure is arranged to be disposed in the second detection path. The spectrometer includes a first radiation detector that detects radiation that passes through the selected filter in the first detection path, and a second radiation detector that detects radiation passing through the filter in the second detection path.

30 Claims, 6 Drawing Sheets

(51) Int. Cl.
*G01J 3/12* (2006.01)
*G01N 21/35* (2014.01)
*G01N 21/31* (2006.01)

(56) References Cited

U.S. PATENT DOCUMENTS

| | | | | |
|---|---|---|---|---|
| 4,447,725 | A | * | 5/1984 | Biggs et al. .............. 250/339.12 |
| 5,464,982 | A | | 11/1995 | Drucker |
| 6,111,563 | A | * | 8/2000 | Hines ............................ 345/166 |
| 6,429,936 | B1 | | 8/2002 | Scaduto |
| 6,486,474 | B1 | | 11/2002 | Owen |
| 6,791,086 | B2 | | 9/2004 | Russell |
| 7,235,054 | B2 | | 6/2007 | Eckerbom |
| 2005/0134854 | A1 | * | 6/2005 | Aguirre et al. ................ 356/416 |

FOREIGN PATENT DOCUMENTS

| | | |
|---|---|---|
| WO | 9404893 A1 | 3/1994 |
| WO | 9525950 | 9/1995 |

* cited by examiner

FILTER WHEEL SPECTROMETER

CROSS REFERENCE TO PRIOR APPLICATIONS

This application is a Divisional application of U.S. Ser. No. 13/128,799, filed May 11, 2011, which is a U.S. National Phase application under 35 U.S.C. §371 of International Application No. PCT/IB2009/054860, filed Nov. 2, 2009, which claims the benefit of U.S. Provisional Patent Application No. 61/115,757, filed Nov. 18, 2008

BACKGROUND OF THE INVENTION

1. Field of the Invention

The present invention pertains to spectrometers, and, more particularly, to a filter wheel and a spectrometer using the filter wheel.

2. Description of the Related Art

Gas analyzers such as spectrometers are widely used in medical applications to measure concentration of carbon dioxide, oxygen gas and anaesthesia agents such as halothane (2-bromo-2-chloro-1,1,1-trifluoroethane), enflurane (2-chloro-1,1,2,-trifluoroethyl-difluoromethyl ether), isoflurane (2-chloro-2-(difluoromethoxy)-1,1,1-trifluoro-ethane), sevoflurane (2,2,2-trifluoro-1-[trifluoromethyl]ethyl fluoromethyl ether), and desflurane (2,2,2-trifluoro-1-fluoroethyl-difluoromethyl ether) during patient anaesthesia. There are two main types of gas analyzers, gas analyzers that are located either in the main path of a patient's respiratory gases (main flow measuring gas analyzers or main stream gas analyzers) or lateral flow measuring gas analyzers. The lateral flow measuring analyzers take a sample from the respiratory circuit of a patient to an adjacent instrument wherein actual gas analysis is performed. On the other hand, main flow or mainstream measuring analyzers calculate gas concentration directly in the respiratory circuit of the patient. Typically, the main flow analyzer is positioned in close proximity of a patient's mouth or trachea. The main flow gas analyzers or spectrometers incorporate the optical and electronic components of the spectrometer in one housing. As a result, in a clinical setting, it is desirable that the mainstream gas analyzers be as compact and lightweight as possible.

Respiratory gas can be analyzed using different methods, including dispersive and non-dispersive spectroscopy. The most common method of gas analysis is based on non-dispersive spectroscopy wherein gases absorb radiation energy (e.g., infrared energy) at a wavelength specific to the gas of concern (e.g., carbon dioxide). A light beam from a light source (e.g., infrared light source) is passed through a patient's respiratory circuit. The light beam that passes through the respiratory circuit is absorbed at various spectral regions specific to the gas in the respiratory circuit of the patient. A detector assembly is positioned on an opposite side of the respiratory circuit of the patient. The detector assembly includes a detector for measuring light intensity and a bandpass filter. The bandpass filter is positioned such that the light beam will pass through the filter before reaching the detector. The bandpass filter can be selected to filter out undesired regions of the wavelength spectrum in the light beam and transmit a spectral region of interest corresponding to an absorption region of the gas in the respiratory circuit of the patient.

While conventional mainstream analyzers may operate well for a small number of specific, non-overlapping spectrum wavelengths (e.g. in the analysis of individual gases such as carbon dioxide), this type of system has had some limitations. For example, the conventional mainstream analyzers can become inefficient for the analysis of a plurality of gases wherein more than 2 or 3 wavelength regions may be involved requiring the use of a plurality of filters.

SUMMARY OF THE INVENTION

An aspect of the present invention is to provide a filter wheel for use in a spectrometer. The filter wheel includes a body having a base and a sidewall connected to the base. The body is configured to be rotatable about an axis of rotation. The filter wheel further includes a plurality of radiation filters disposed on the base, and a plurality of radiation filters disposed on the sidewall.

Another aspect of the present invention is to provide a spectrometer including a filter wheel having a body comprising a base and a sidewall, the body configured to be rotatable about an axis of rotation. A plurality of radiation filters disposed on the base, and a plurality of radiation filters disposed on the sidewall. The spectrometer further includes a first radiation detector arranged to detect radiation received by the filters disposed on the base, and a second radiation detector arranged to detect radiation received by the filters disposed on the sidewall. The spectrometer also includes at least one radiation beam splitter configured to split a beam of radiation into a first radiation beam portion and second radiation beam portion so that the first radiation beam portion is received by the first radiation detector and the second radiation beam portion is received by the second radiation detector.

Another aspect of the present invention is to provide a spectrometer including a radiation source capable of generating a radiation beam, a beam splitter that receives the radiation beam and splits the radiation beam into a first detection path and a second detection path, and a filter wheel. The filter wheel has a first support structure on which a first plurality of filters are mounted and a second support structure on which at least one filter is provided. The first plurality of filters are selectively movable into the first detection path. The at least one filter on the second support structure is arranged to be disposed in the second detection path. The spectrometer further includes a first radiation detector arranged to detect radiation that passes through the selected filter in the first detection path, and a second radiation detector arranged to detect radiation that passes through the filter in the second detection path.

Yet another aspect of the present invention is to provide a spectrometer including a housing, a rotatable body disposed in the housing, a spindle mounted to the housing, and a plurality of seating cups mounted within the housing, and between which the spindle is rotatably held. A plurality of filters are disposed on the rotatable body. The plurality of filters are structured to transmit desired wavelength ranges of radiation.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various FIGS. In one embodiment of the invention, the structural components illustrated herein are drawn to scale. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EMBODIMENTS OF THE INVENTION

Figure 1:
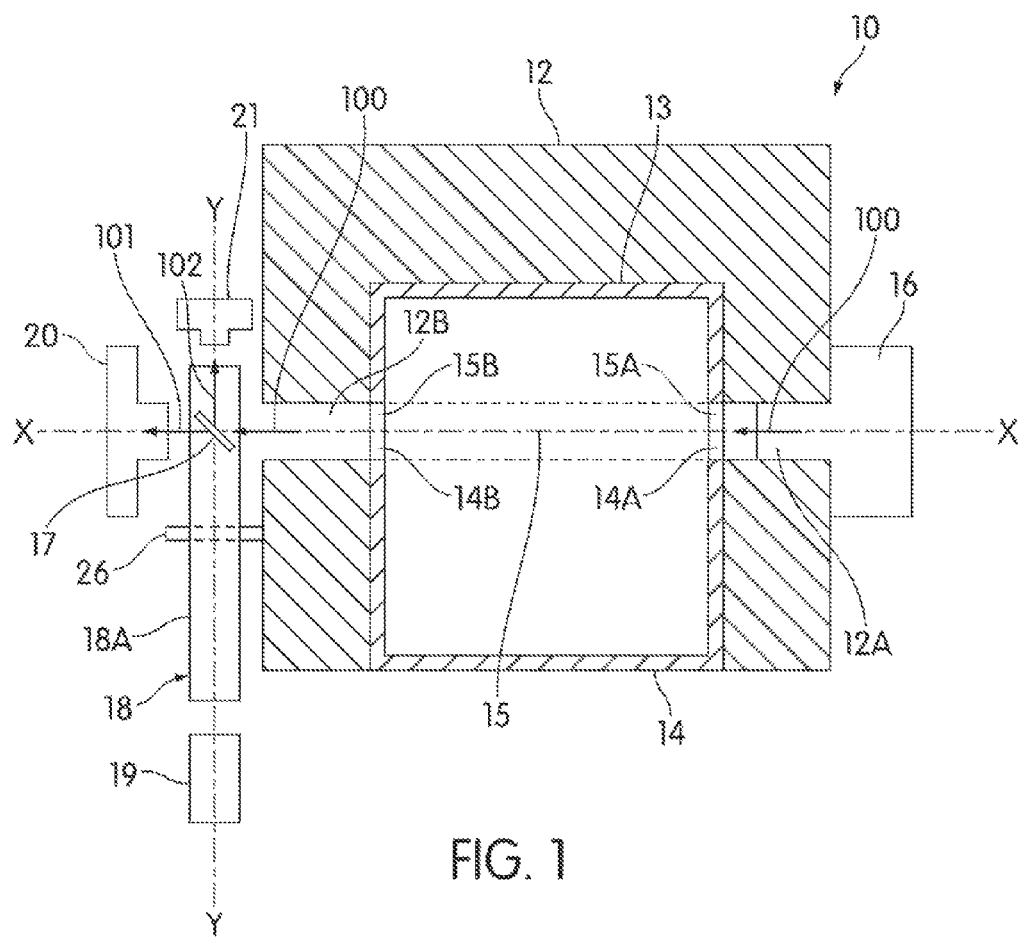
FIG. 1 is a schematic representation of a spectrometer, according to an embodiment of the present invention.

FIG. 1 is a schematic representation of a spectrometer 10, according to an embodiment of the present invention. Spectrometer 10 includes a housing 12 having an aperture 13 adapted to receive a conduit or airway adapter 14 so as to connect housing 12 to airway adapter 14. Airway adapter 14 can be connected to tubing or a further conduit (not shown) that leads to a patient respiratory tract such as the mouth or nose of the patient. Airway adapter 14 can also be connected to a breathing apparatus (not shown) such as a ventilator to assist a patient in breathing. Housing 12 includes two opposite openings 12A and 12B directly communicating with, respectively, two opposite window covered openings 14A and 14B provided in the airway 14. Openings 12A, 12B, 14A and 14B are aligned along a same axis X-X. Windows 15A, 15B are mounted to airway 14 to hermetically seal lateral openings 14A and 14B, respectively, in airway adapter 14 so that gas in the airway does not escape through lateral openings 14A and 14B.

Spectrometer 10 also includes a radiation source 16 for emitting radiation (e.g., infrared light), a beam splitter 17, a filter wheel 18, a motor assembly 19, and radiation detectors 20 and 21. Radiation source 16, beam splitter 17, filter wheel 18 and radiation detectors 20 and 21 can optionally be mounted to housing 12. Radiation source 16 can be mounted on one side of housing 12 such that light emitted by the radiation source 16 is directed towards opening 12A of housing 12. Alternatively, radiation source 16 may not be mounted to housing 12 and can be provided separate from the housing, for example outside spectrometer 10. In one embodiment, an optical fiber, for example, can be used to guide the light from radiation source 16 towards opening 12A of housing 12. Radiation source 16 can include a radiation emitter such as an infrared emitting diode and a control circuit for controlling the radiation emitter.

Filter wheel 18 is rotatable. In one embodiment, the filter wheel may be rotatably mounted to housing 12. Motor assembly 19 is configured to rotate filter wheel 18. Beam splitter 17 is disposed within the filter wheel adjacent to or facing opening 12B in housing 12, as will be described further in detail in the following paragraphs. Radiation detector 20 is disposed on an opposite side of housing 12 opposite filter wheel 18 and facing opening 12B in housing 12 along an axis X-X. Radiation detector 21 is disposed along an axis Y-Y substantially perpendicular to axis X-X and facing a sidewall of filter wheel 18. Radiation detectors 20 and 21 can be mounted, for example, to housing 12 or mounted to a cover (not shown) of spectrometer 10. Alternatively, the radiation detector can be provided separate from spectrometer 10, in which case optical fibers may be used to guide light that exits filter wheel 18 to radiation detectors 20, 21.

Radiation detectors 20 and 21 include a radiation sensor, a biasing and amplification circuit and a signal processing unit for amplifying and processing an electrical signal output by the radiation sensor. In one embodiment, radiation detector 20 is selected to detect in the mid-infrared (mid-IR) region of the spectrum (e.g., between about 3 μm and about 8 μm) and radiation detector 21 is selected to detect in the infrared region (IR) of the spectrum (e.g., between about 7 μm to about 15 μm). In one embodiment, radiation detector (mid-IR) 20 comprises a lead selenide (PbSe) sensor. In one embodiment, radiation detector (IR) 21 comprises a pyroelectric sensor. Examples of the type of radiation detectors that may be employed herein are described, for example, in U.S. Pat. No. 7,235,054 to Eckerbom issued on Jun. 26, 2007, U.S. Pat. No. 6,486,474 to Owen et al. issued on Nov. 26, 2002, and U.S. Pat. No. 5,464,982 to Drucker et al. issued on Nov. 7, 1995, the entire contents of each of which are incorporated herein by reference.

Figure 2:
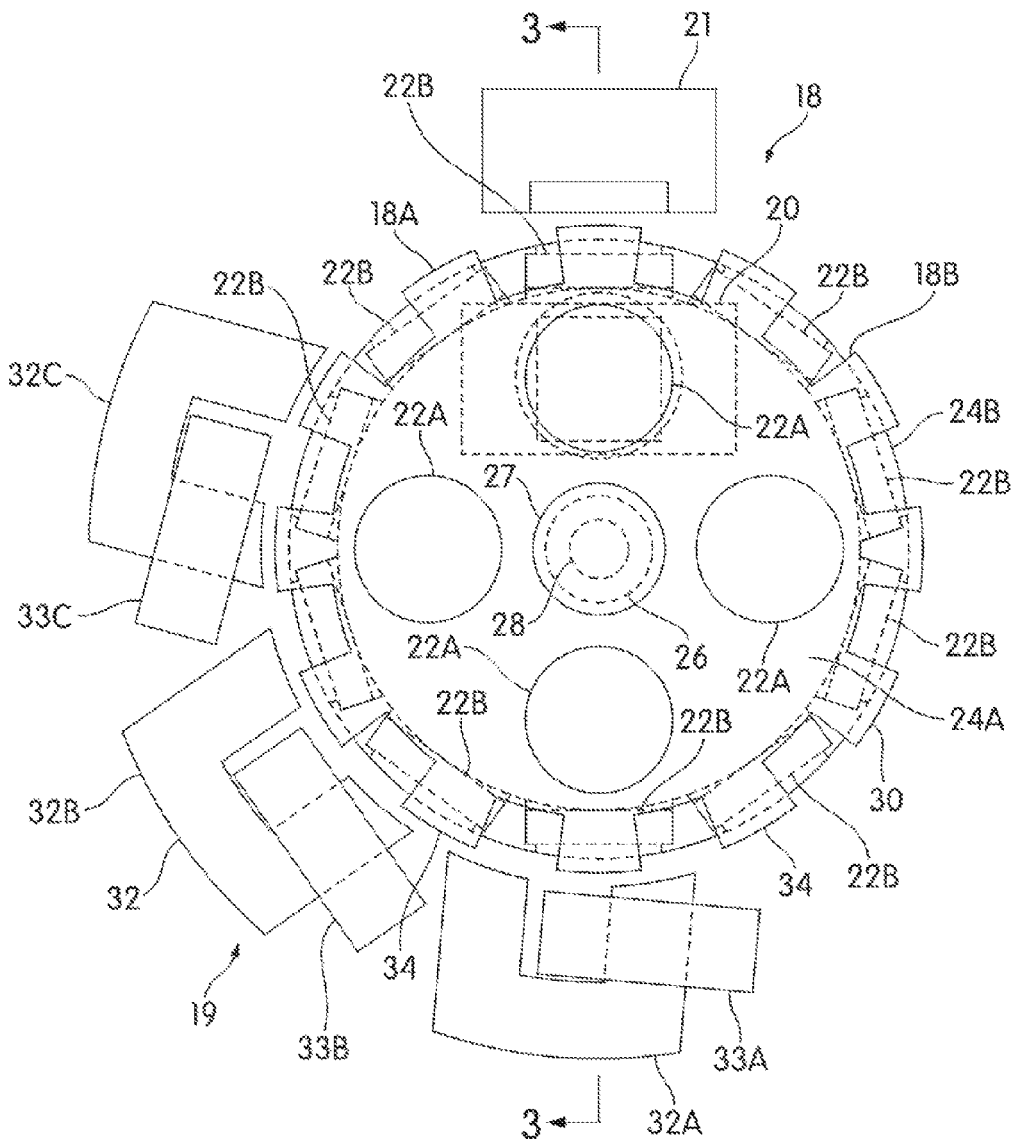
FIG. 2 is a schematic front view of a filter wheel, according to an embodiment of the present invention.
Figure 3:
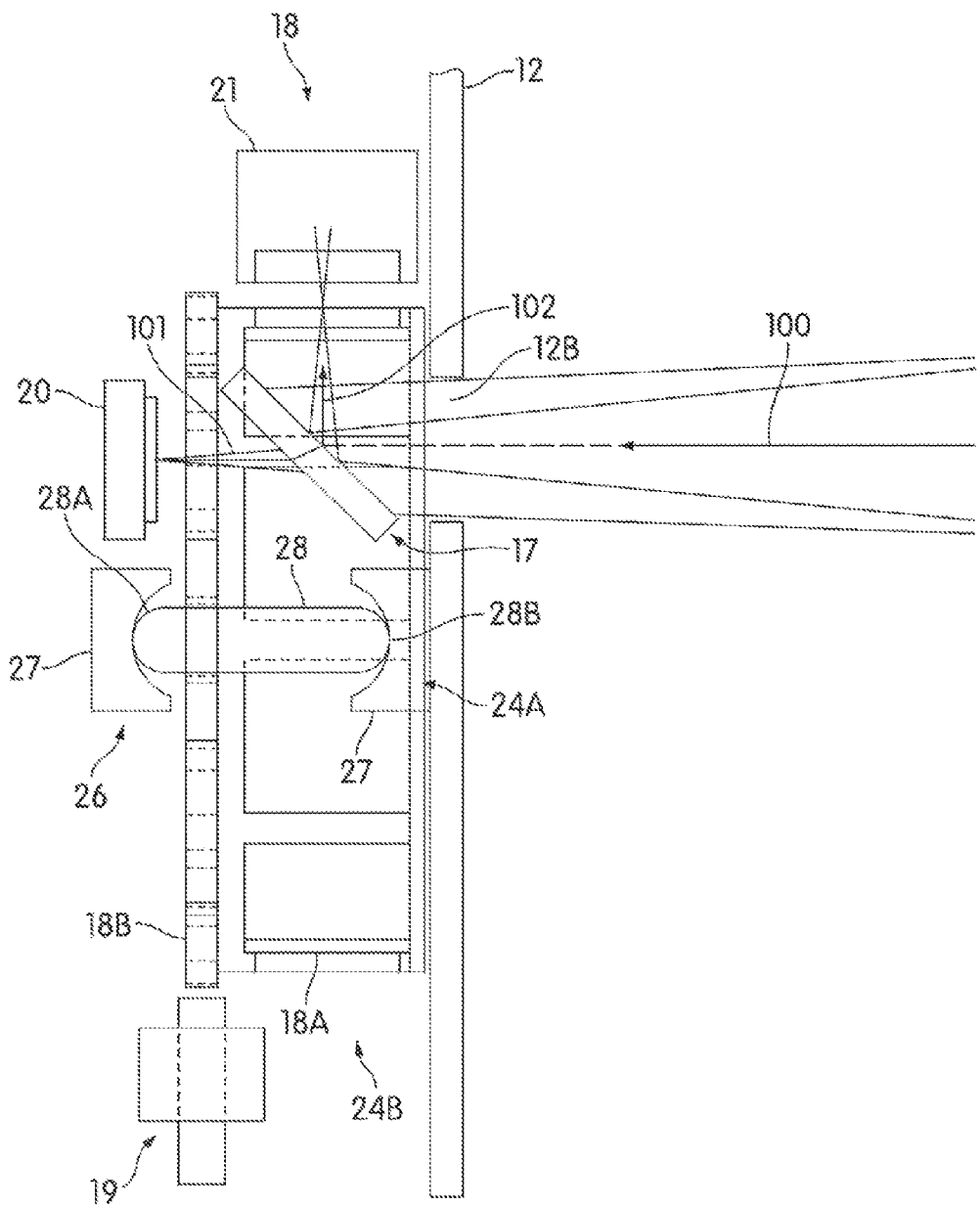
FIG. 3 is a cross-sectional view of the filter wheel along the cross-section BB, as shown in FIG. 2.

FIG. 2 is a schematic front view of filter wheel 18, according to an embodiment of the present invention. FIG. 3 is a cross-sectional view of filter wheel 18 along the cross-section B-B shown in FIG. 2. In one embodiment, filter wheel 18 has a body 18A including a circular base 24A and an annular sidewall 24B connected to base 24A. Base 24A and the sidewall can be constructed as separate pieces or can be integrally formed as one-piece. For example, base 24A and sidewall 24B of filter wheel 18 can be integrally formed from plastic in an injection molding process. In one embodiment, filter wheel 18 has a cylindrical shape such as a drum-shape or wheel-shape. Filter wheel 18 comprises a plurality of filters 22A and a plurality of filters 22B. Filters 22A are disposed at openings in base 24A of the cylinder (face of the drum) filter wheel 18. Filters 22B are disposed at openings in the sidewall 24B of the cylinder (rim of the drum) filter wheel 18.

In one embodiment, filters 22A disposed on the base 24A are azimuthally spaced apart with the same angle around the axis of rotation of filter wheel 18. In one embodiment, filters 22B are equidistantly spaced apart around the sidewall 24B. In an alternate embodiment, filters 22A can be spaced azimuthally at different angles and/or filters 22B can be spaced apart with the same distance or different distances.

Filters 22A can have the same size and/or shape or different sizes and/or shapes. Similarly, filters 22B can have the same size and/or shape or different sizes and/or shapes. In one embodiment, one or more filter (e.g., filter 22A or filter 22B) can be sized or shaped to expand and occupy the position of two or more filters (e.g., filters 22A or filters 22B). Such an arrangement removes the signal interruption and signal loss caused by the opaque filter wheel body. In this case, light can be transmitted through the "expanded" filter during a time period double, triple or more the time period of other filters (filters 22A or filters 22B) in filter wheel 18, hence providing a longer signal integration time which can improve a signal-to-noise ratio for that expanded filter.

In one exemplary embodiment, four (4) filters 22A are provided on base 24A of filter wheel 18 and ten (10) filters 22B are provided on sidewall 24B of the filter wheel. However, as it can be appreciated, any number of filters 22A can be provided on base 24A and any number of filters 22B can be provided on sidewall or rim 24B of filter wheel 18. Although, filter wheel 18 is depicted herein having a cylindrical shape with a generally circular base, other shapes are also within the scope of the present invention. For example, the filter wheel 18 can have a cylindrical shape with a polygonal (e.g., triangular, square, hexagonal, octagonal, decagonal, etc.) base shape. For example, in the case of a cylindrical shape with a decagonal base, each of the 10 filters 22B can be positioned on each face of the 10 sidewalls of the decagonal base-shaped cylinder.

In one embodiment, two filters 22A are selected to transmit in the mid-infrared (mid-IR) region of the spectrum in the absorption spectrum of carbon dioxide ($CO_2$). In one embodiment, the spectral region of transmission of the two $CO_2$ filters 22A is selected to be between about 3.5 µm and about 5 µm. A narrower spectral band may also be used if desired such as a narrow spectral band centered around 4.25 µm for the $CO_2$ filters 22A. Another filter 22A can be selected to transmit in a spectral band centered around 4.56 µm in the absorption spectrum of nitrous oxide ($N_2O$). Yet another filter 22A can be selected to transmit in a spectral band centered around 3.69 µm in the absorption spectrum of a reference substance. In one embodiment, the reference substance can be a calibrated amount of $CO_2$.

In one embodiment, filters 22B on sidewall 24B of wheel 18 can be used to transmit various wavelength regions in the absorption spectrum of various chemical agents such as, but not limited to, anaesthesia agents (e.g., halothane, enflurane, isoflurane, sevoflurane, and desflurane) or other medications. In one embodiment, ten (10) filters 22B are provided on sidewall 24B of filter wheel 18. Each bandpass filter 22B can be selected to transmit in one absorption spectral region specific to one or more of the chemical agents. Alternatively, one or more filters 22B can be identical to each other and transmit the same spectral region. Absorption peaks of various chemical agents of interest lie in the wavelength range between about 7 µm and about 15 µm. The most intense absorption peaks occur between 7 µm and 10.2 µm. In one embodiment, the five (5) chemical agents of interest, such as halothane, enflurane, isoflurane, sevoflurane, and desflurane, for example, have about nine (9) absorption peaks between about 7 µm and about 10.2 µm. There are several possible filter combinations that can be implemented. One possible filter selection can be a series of bandpass filters with a wavelength transmission centered around the 9.65 µm, 9.10 µm, 8.60 µm, 8.20 µm, and 8.00 µm. If measurement of more chemical agents is needed, more bandpass filters can be added or substituted as desired.

Although, filters 22A that are positioned on base 24A of filter wheel 18 are described above as being filters that transmit in the mid-IR (e.g., between about 3 µm and about 8 µm) and filters 22B that are disposed on sidewall 24B of filter wheel 18 are described above as filters that transmit in the IR range (e.g., between about 7 µm to about 15 µm), it can be appreciated that filters 22A and 22B can be interchanged. For example, filters 22A that transmit in the mid-IR (e.g., between about 3 µm and about 8 µm) can be positioned on sidewall 24B of filter wheel 18 while filters 22B that transmit in the IR (e.g., between about 7 µm to about 15 µm) can be positioned on base 24A of the filter wheel. In addition, in another embodiment, for example, filters that transmit visible light can be disposed on base 24A of filter wheel 18 while mid-IR and/or other IR ranges transmitting filters can be disposed on sidewall 24B of the filter wheel.

In one embodiment, filter wheel 18 is rotatably mounted to housing 12 via a bearing structure 26. In one embodiment, bearing structure 26 is a cup and ball type system comprising two curved seating cups 27 and an elongated spindle 28 having two rounded or semi-spherical ends 28A and 28B. Elongated spindle 28 is rotatably held between the two seating cups 27. Specifically, rounded spherical ends 28A and 28B of elongated spindle 28 are brought in contact with the concave surface of the two seating cups 27. Seating cups 27 can be mounted to housing 12 and a cover (not shown) of spectrometer 10 and elongated spindle 28 can be mounted to filter wheel 18 to define an axis of rotation of the filter wheel. For example, in one embodiment, base 24A of filter wheel 18 can be mounted to elongated spindle 28 while sidewall 24B, which is connected to base 24A, may or may not be connected to spindle 28.

Bearing structure 26 can provide a low friction rotation system. In addition, bearing structure 26 can provide self-centering of filter wheel 18. Furthermore, filter wheel 18 can tolerate shock, as spindle 28 will tend to self align within seating cups 27. Although a cup and ball type system is illustrated herein, it can be appreciated that other types of bearing systems can be used such as magnetic bearings or rolling element bearings or ball bearings, etc.

Although filter wheel 18 including base 24A and sidewall 24B are described herein as being rotatably mounted to housing 12 via bearing structure 26, it can be appreciated that, in another embodiment, base 24A can be rotatably mounted to bearing structure 26 (e.g., mounted to spindle 28) while sidewall 24B can be independently mounted to another structure (e.g., fixedly mounted to another structure or rotatably mounted to another structure) or sidewall 24B can be omitted.

Filter wheel 18 comprises an armature portion 18B. Armature portion 18B is mounted to a periphery of body 18A of filter wheel 18. Motor 19 is used to rotate filter wheel 18. In one embodiment, motor 19 is a stepping motor, such as a modified variable reluctance three phase motor. Motor 19 comprises a rotor portion 30 and a stator portion 32. Rotor portion 30 is part of armature portion 18B of filter wheel 18. Rotor portion 30 is configured to interact with stator portion 32 of motor 19 to rotate filter wheel 18 about an axis defined by spindle 28. Rotor portion 30 comprises a plurality of teeth or projections 34. The plurality of teeth or projections 34 act as rotor poles.

In one embodiment, teeth 34 can be made from a magnetic or magnetizable material such as soft iron or a material comprising soft iron such as silicon steel. The plurality of teeth or projections 34 in rotor portion 30 act as salient magnetic poles through magnetic reluctance and magnetically interact with a stator portion 32 of motor 19. Stator portion 32 comprises a plurality of stator coils or stator poles 32A, 32B and 32C spaced around the rotor portion 30. In one embodiment, stator coils 32A, 32B and 32C include electrical stator winding 33A, 33B and 33C for energizing the stator coils 32A, 32B and 32C, respectively. In the illustrated embodiment, three (3) stator coils or stator poles 32A, 32B and 32C are used. However, it can be appreciated that two (2) or more stator poles can be used.

When a rotor pole, i.e., a tooth or projection 34 in rotor portion 30, is equidistant from two adjacent stator poles or stator coils 32A and 32B, for example, rotor pole 34 is in a fully unaligned position. In this position, maximum magnetic reluctance is achieved for the rotor pole 34. When two or more rotor poles 34 are aligned with, i.e., facing, the two or more stator poles, minimum magnetic reluctance is achieved. When a stator pole (for example stator pole 32A) is energized a rotor torque develops in the direction that will reduce magnetic reluctance. As a result, the nearest rotor pole 34 is pulled from the unaligned position into alignment with the stator pole 32A (a position of minimum reluctance).

Figure 4A:
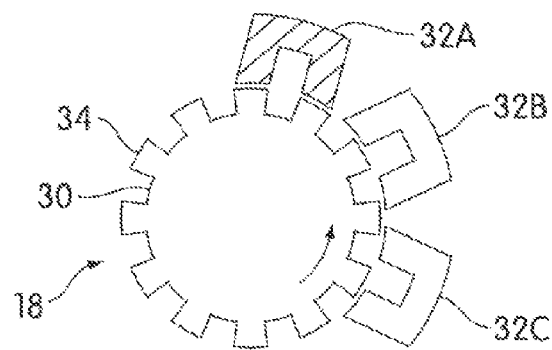
FIGS. 4A, 4B and 4C depict a sequential energizing of stator poles of a motor for rotating the filter wheel, according to an embodiment of the present invention.
Figure 4B:
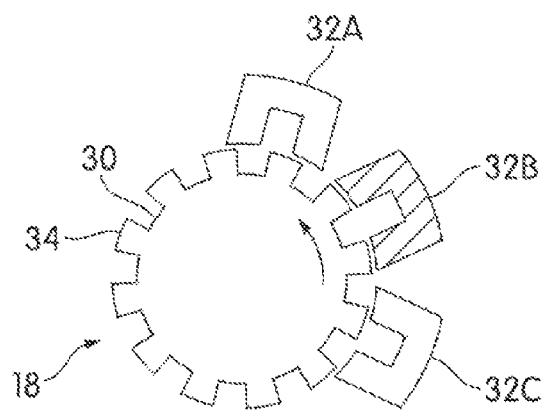
Figure 4C:
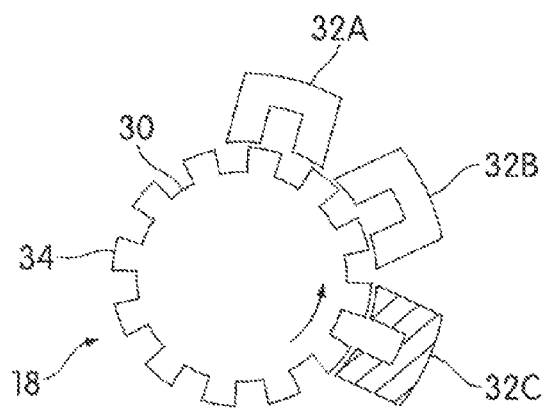

In order to sustain continued rotation, stator coils or poles 32A, 32B and 32C (in the case of a motor comprising 3 stator coils) are arranged such that when one stator pole (e.g., stator pole 32A) is facing or is in alignment with the rotor poles 34, the other two stator poles (e.g., stator poles 32B and 32C) are not facing or only partially facing, i.e., are in misalignment with, rotor poles 34. In this way, as depicted in FIGS. 4A, 4B and 4C, when stator poles 32A, 32B and 32C are sequentially energized in a 3-phase electrical configuration, rotor poles 34 will sequentially align with the energized stator poles 32A, 32B and 32C. Specifically, when stator pole 32A is energized in a first phase, as illustrated in FIG. 4A with hatched lines, the projections or rotor poles 34 of rotor portion 30 become aligned with the stator pole 32A while other rotor poles 34 in rotor portion 30 are misaligned with the stator poles 32B and 32C. When the stator pole 32B is energized in a second phase, as illustrated in FIG. 4B with hatched lines, the projections or rotor poles 34 of rotor portion 30 become aligned with stator pole 32B while other rotor poles 34 in rotor portion 30 are misaligned with the stator poles 32A and 32C, thus forcing the rotor portion 30 to move counter clockwise. When the stator pole 32C is energized in a third phase, as illustrated in FIG. 4C with hatched lines, the projections or rotor poles 34 of rotor portion 30 become aligned with stator pole 32C while other rotor poles 34 in rotor portion 30 are misaligned with stator poles 32B and 32C thus further forcing rotor portion 30 to move counter clockwise. By sequentially energizing stator poles 32A, 32B, 32C, rotor poles 34 of rotor portion 30 (and thus the filter wheel 18) will rotate counter clockwise, as shown by the arrows in FIGS. 4A, 4B and 4C.

In one embodiment, motor 19 is configured (e.g., the electronic driver of the motor is configured) so as to keep detector(s) 20 and/or 21 serially synchronized with the rotation of filter wheel 18. In one embodiment, motor 19 does not provide an indication of the rotation of the filter wheel relative to a reference point (e.g., the motor does not provide a "start" or "filter one" reference indication). Hence, in one embodiment, in order to provide a reference point so as to synchronize detector(s) 20 and/or 21 to the rotation of filter wheel 18, the location of one of filters 22A and/or one of filters 22B positions can be blanked off. In this way, a zero detector signal detected by the detector 20 and/or 21 when the blanked filter position is in the path of light, in conjunction with the drive pulses of the motor 19 and the sequence of "on" signals to the various phases of motor 19 can define the location of the filter wheel 18, i.e., the location of each filter in the filter wheel 18. In addition to providing synchronization between the rotation of filter wheel 18 and detectors 20 and 21, the blanked off position can also be used to provide a signal offset test to detectors 20 and 21.

In an alternative embodiment, instead or in addition to using a blanked filter position, a small magnet can be placed on one of the plurality of teeth 34 so that a back-electromagnetic force (back-emf) can be generated on a specific stator pole 32A, 32B or 32C, as the magnet moves past the stator. Alternatively, the magnet can also be placed with poles perpendicular to a plane of armature portion 18B of filter wheel 18, anywhere on armature portion 18B, and a separate pickup coil above or below the magnet can be used to sense when the magnet passes by during the rotation of armature portion 18B (i.e., during the rotation of the filter wheel 18).

In yet another alternative embodiment, a small hole can be placed in the base 24A of filter wheel 18, in sidewall 24B of filter wheel 18, or armature 18B of filter wheel 18 (inside of the tooth radius) so that a conventional light emitting diode (LED) can be used to direct light through the hole to an additional separate photodetector positioned to receive the light and thus provide a reference point. In essence, any device capable of providing a reference signal (reference point) can be used.

Although, filter wheel 18 is shown rotating in a counter clockwise direction, a rotation in the clockwise direction can also be achieved by energizing stator poles 32A, 32B and 32C in a reverse sequence, i.e., energizing stator pole 32C in phase 1, stator pole 32B in phase 2 and stator pole 32C in phase 3. Furthermore, although motor 19 is described herein operating in a tri-phase configuration, the motor can also be selected to operate in a two-phase configuration. In the two-phase configuration, there is no inherent start direction. Therefore, teeth 34 can be shaped or shading bars added to armature portion 18B of filter wheel 18 to define the start direction. Alternatively, logic can be added to the detectors circuitry to determine which direction the filter wheel is rotating.

In operation, radiation beam 100 emitted by radiation source 16 is directed towards opening 12A of housing 12 to be transmitted through the window in opening 14A in airway adapter 14. Radiation beam 100 that passed through window 15A in opening 14A passes through a central portion 15 of airway adapter 14, then through window 15B in opening 14B to exit through opening 12B in housing 12. Windows 15A and 15B in openings 14A and 14B are selected from a material so as to be substantially transparent at wavelengths of radiation of interest (e.g., between about 3 μm and about 15 μm) in the radiation emitted by the radiation source 16. A spectral portion of radiation beam 100 is absorbed by molecules (e.g., $CO_2$, $N_2O$, or other chemical substances, or any combination of two or more thereof) that are present in airway adapter 14.

Radiation beam 100 exiting from opening 12B is split by beam splitter 17 disposed within filter wheel 18 into two radiation beams 101 and 102. In one embodiment, beam splitter 17 splits radiation beam 100 into two beams 101 and 102 in two spectral regions without substantially any energy loss. In another embodiment, beam splitter 17 splits radiation beam 100 into two beam portions 101 and 102 (e.g., having approximately equal intensity) without splitting the spectrum of beam 100 into two spectral regions. In this instance, a conventional relatively non-expensive semi-reflecting or semi-transparent mirror at the radiation of interest can be used as a beam splitter 17. Radiation beam 101 is directed along the X-X axis towards one of filters 22A disposed on the base 24A of filter wheel 18 and radiation beam 102 is directed along the axis Y-Y perpendicular to the axis X-X towards one of filters 22B disposed on sidewall 24B of filter wheel 18. Radiation beam 101 passes through one of the filters 22A in filter wheel 18 before reaching radiation detector 20. Radiation beam 102 passes through one of the filters 22B in filter wheel 18 before reaching radiation detector 21.

Filter 22A filters out a portion of a wavelength spectrum of radiation beam 101 and transmits a portion of the wavelength spectrum centered around a wavelength region of interest (for example a region in the absorption spectrum of $CO_2$ or $N_2O$). Similarly, filter 22B filters out a portion of a wavelength spectrum of radiation beam 102 and transmits a portion of the wavelength spectrum centered around a wavelength region of interest (for example a region in the absorption spectrum of a chemical agent such as halothane). Hence, the geometry of filter wheel 18 coupled with the use of a spectral beam splitter 17, allows the use of two (2) separate detectors 20 and 21 for detecting two spectral regions, each detector being dedicated to detect one spectral region (e.g., mid-IR and IR). By rotating filter wheel 18, a desired filter 22A in the filter wheel can be selected to transmit a desired portion of the wavelength spectrum (for example a region in the absorption spectrum of $CO_2$) in radiation beam 101. Similarly, by rotating filter wheel 18, a desired filter 22B in the filter wheel can be selected to transmit a desired portion of the wavelength spectrum (for example a region in the absorption spectrum of halothane) in radiation beam 102.

In an alternate embodiment, filter wheel 18 can be constructed such that base 24A of the filter wheel is rotatable while sidewall 24B of the filter wheel is fixed. Alternatively, filter wheel 18 can also be constructed such that sidewall 24B of the filter wheel is rotatable while base 24A of the filter wheel is fixed. In this way, base 24A or sidewall 24B of filter wheel 18 can be independently rotated from the other if desired.

In one embodiment, beam splitter 17 is mounted to a movable mount (not shown). The movable mount can be a motorized or a mechanically movable mount. The movable mount enables beam splitter 17 to be moved out of the path of the radiation beam 100. When beam splitter 17 is moved out of the path of radiation beam 100, the radiation beam will not be split into two beams 101 and 102. In this case, radiation beam 100 continues in its path along the X-X axis towards one of filters 22A disposed on base 24A of the filter wheel before reaching radiation detector 20 in the same manner as described in U.S. Pat. No. 7,235,054 to Eckerbom, the entire contents of which are incorporated herein by reference.

In the case where two filters 22A are selected to transmit in the mid-infrared (mid-IR) region of the absorption spectrum of carbon dioxide ($CO_2$), the absorption of $CO_2$ is measured twice within a complete revolution, i.e. 360 degrees rotation, of the filter wheel 18, in principle. The absorption of $CO_2$ is measured every 180 degrees rotation of the filter wheel 18. On the other hand, if each of the ten (10) filters 22B is selected to transmit in the IR region of the absorption spectrum of a specific chemical agent (e.g. halothane), the absorption of the specific chemical agent is measured once every revolution, i.e., once every 360 degrees rotation, of filter wheel 18, in principle. If each of filters 22B is used to measure the absorption of each of the chemical agents, the filter wheel is rotated by a 36 degree step, i.e., 360 degrees divided by the number of filters 22B (e.g., 10). Hence, an amount of energy collected by the $CO_2$ molecules in airway adapter 14 is equal to 5 (180 degrees rotation for each $CO_2$ filter 22A divided by 36 degrees rotation for each agent filter 22B) times the amount of energy collected by a chemical agent. As a result, the signal-to-noise ratio for $CO_2$ absorption measurement is better than the signal-to-noise ratio for chemical agent absorption measurement, other parameters being equal. In general, the ratio between an amount of energy collected by the $CO_2$ molecules and an amount of energy collected by the chemical agent is equal to m/n, where m is the number of agent filters 22B and n is the number of filters 22A for a molecule of interest (e.g., $CO_2$). For example, in the case of $N_2O$, where only one filter 22A is used, the ratio between an amount of energy collected by $N_2O$ molecules and an amount of energy collected by a chemical agent is equal to 10, in principle.

In one embodiment, the filter wheel can be configured to rotate at a rotation speed between about 2000 RPM and about 3000 RPM. For example, a rotation speed of about 3000 RPM provides a sample rate for measuring $CO_2$ absorption of about 50 samples/second. In general, a sample rate for $CO_2$ can be between about 50 samples/second and about 100 samples/second so that a response time for a patient breath can be at least 10 cycles/second as the average breathing rate for most healthy people is in the range of 10 to 18 breaths per minute. If two or more $CO_2$ filters 22A are used, the speed of rotation can be reduced, for example divided by 2, to a value between about 1000 RPM and about 1500 RPM. The response time for the other chemicals or agents can be one cycle/second or less, thus allowing a much slower sampling rate than the sampling rate of $CO_2$.

Figure 5:
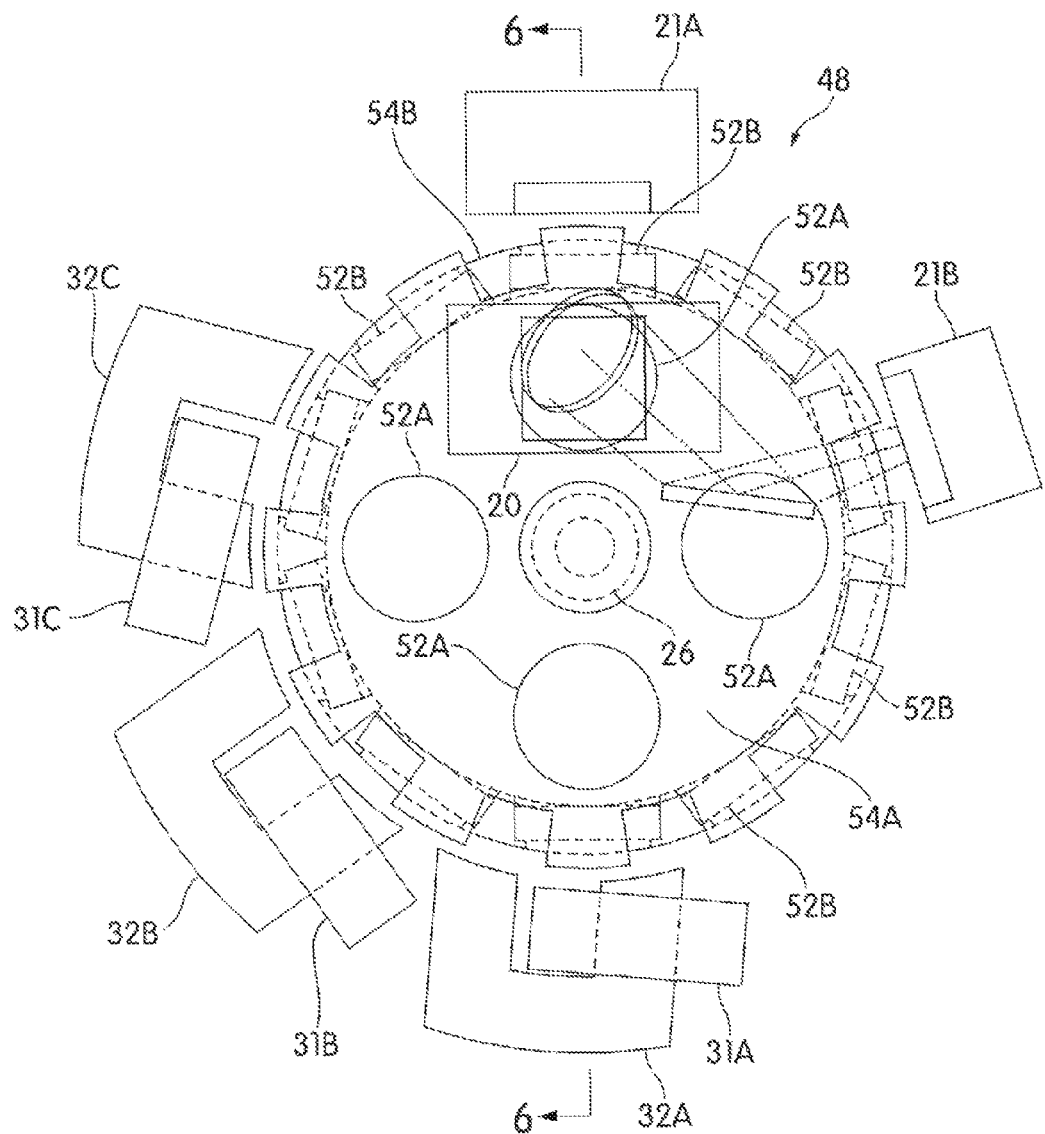
FIG. 5 is a schematic front view of a filter wheel, according to another embodiment of the present invention.
Figure 6:
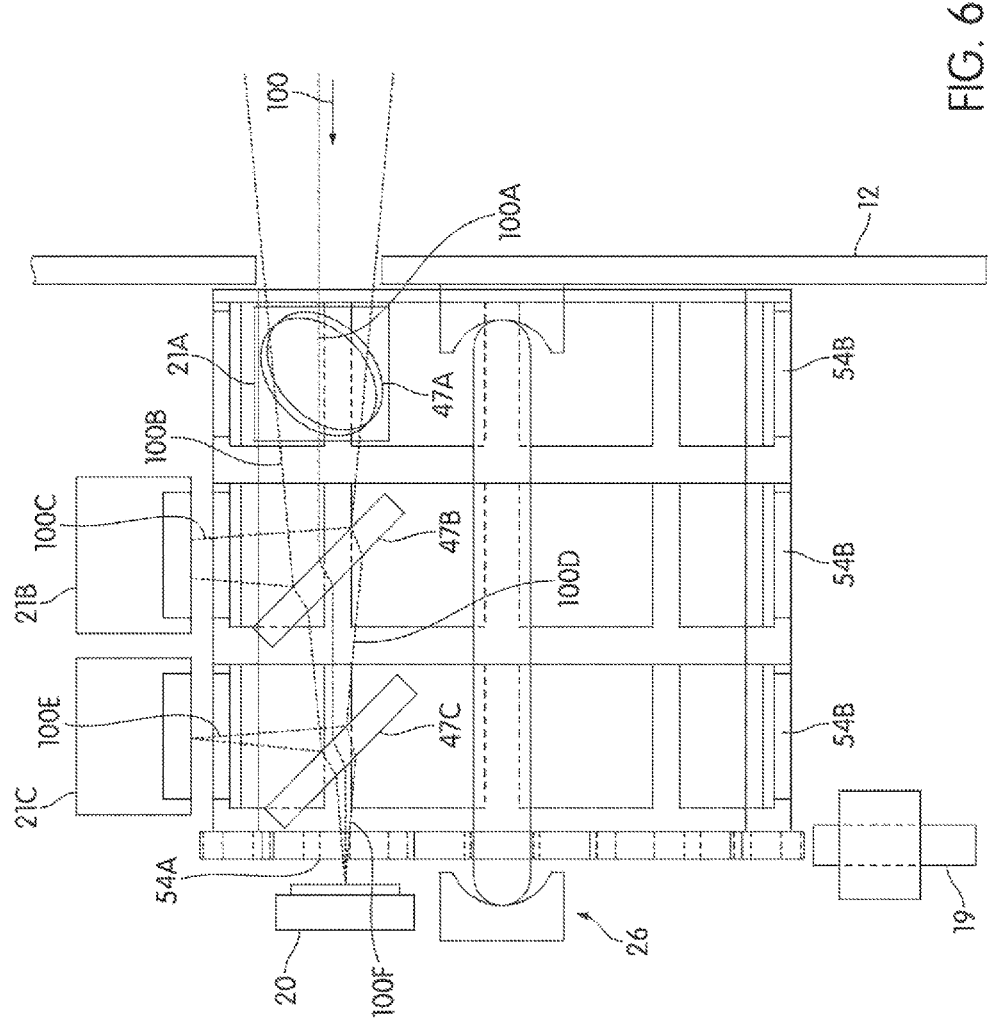
FIG. 6 is a cross-sectional view of the filter wheel along the cross-section BB, as shown in FIG. 5.

FIG. 5 is a schematic front view of a filter wheel 48, according to another embodiment of the present invention. FIG. 6 is a cross-sectional view of the filter wheel 48 along the cross-section BB shown in FIG. 5. Filter wheel 48 is similar in many aspects to filter wheel 18. Filter wheel 48 has a cylindrical shape such as a drum-shape or wheel shape. Filter wheel 48 comprises a plurality of filters 52A and a plurality of filters 52B. Filters 52A are disposed at openings in base 54A of the cylinder (face of the drum) filter wheel 48. Filters 52B are disposed at openings in a sidewall 54B of the cylinder (rim of the drum) filter wheel 48. In one embodiment, filters 52A disposed on base 54A are azimuthally spaced apart with the same angle around the axis of rotation of the filter wheel 48. In one embodiment, filters 52B are equidistantly spaced apart around the sidewall 54B. In an alternate embodiment, filters 52A can be spaced azimuthally at different angles and/or the filters 52B can be spaced apart with the same distance or different distances.

Filters 52A can have the same size and/or shape or different sizes and/or shapes. Similarly, filters 52B can have the same size and/or shape or different sizes and/or shapes. In one embodiment, one or more filter (e.g., filter 52A or filter 52B) can be sized or shaped to expand and occupy the position of two or more filters (e.g., filters 52A or filters 52B). Such an arrangement removes the signal interruption and signal loss caused by the opaque filter wheel body. In this case, light can be transmitted through the "expanded" filter during a time period double, triple or more the time period of other filters (filters 52A or filters 52B) in the filter wheel 48, hence providing a longer signal integration time which can improve a signal-to-noise ratio for that expanded filter.

Similar to the embodiment shown in FIG. 2, four (4) filters 52A are provided on the base 54A of the filter wheel 48 and a plurality of filters 52B are provided on the sidewall 54B of filter wheel 48. However, as it can be appreciated, any number of filters 52A can be provided on base 54A and any number of filters 52B can be provided on the sidewall or rim 54B of the filter wheel 48. However, in this embodiment, the rim or sidewall 54B of filter wheel 48 is wider than the sidewall 24B of filter wheel 18, and thus a greater number of filters 52B can be positioned therein. For example, as shown in FIG. 6, three rows of ten (10) filters 52B can be provided on sidewall 54B of filter wheel 48. Filters 52B in each row in sidewall 54 can be aligned to each other or positioned in a staggered configuration. The staggered configuration can be used, for example, to reduce the width of sidewall 54B.

Although, filter wheel 48 is depicted herein having a cylindrical shape with a generally circular base, other shapes are also within the scope of the present invention. For example, the filter wheel 48 can have a cylindrical shape with a polygonal (e.g., triangular, square, hexagonal, octagonal, decagonal, etc.) base shape. For example, in the case of a cylindrical shape with a decagonal base, each of then (10) filters 52B can be positioned on each of the ten (10) sidewalls of the decagonal base-shaped cylinder for each of the three rows of the sidewall 54B.

Similar to the embodiment depicted in FIG. 2, two filters 52A can be selected to transmit, in the mid-infrared (mid-IR) region of the spectrum in the absorption spectrum of carbon dioxide ($CO_2$). Another filter 52A can be selected to transmit in a spectral band centered around 4.56 μm in the absorption spectrum of nitrous oxide ($N_2O$). Yet another filter 52A can be selected to transmit in a spectral band centered around 3.69

μm in the absorption spectrum of a reference substance. In one embodiment, the reference substance can be a calibrated amount of $CO_2$.

In one embodiment, the filters 52B on sidewall 54B of wheel 48 can be used to transmit various wavelength regions in the absorption spectrum of various chemical agents such as, but not limited to, various anaesthesia agents or chemical agents and medications. Absorption peaks of various chemical agents of interest lie in the wavelength range between about 7 μm and about 15 μm. In one embodiment, three rows of 10 filters 52B are provided on the sidewall 54B of the filter wheel 48. Each bandpass filter 52B can be selected to transmit in one absorption spectral region specific to one or more of the chemical agents. Alternatively, one or more filters 52B can be identical to each other and transmit the same spectral region.

Although, filters 52A that are positioned on base 54A of filter wheel 48 are described above as being filters that transmit in the mid-IR (e.g., between about 3 μm and about 8 μm) and filters 52B that are disposed on sidewall 54B of the filter wheel are described above as filters that transmit in the IR range (e.g., between about 7 μm to about 15 μm), it can be appreciated that filters 52A and 52B can be interchanged. For example, filters 52A that transmit in the mid-IR (e.g., between about 3 μm and about 8 μm) can be positioned on sidewall 54B of filter wheel 18, while filters 52B that transmit in the IR (e.g., between about 7 μm to about 15 μm) can be positioned on base 24A of the filter wheel. In addition, in another embodiment, for example, filters that transmit visible light can be disposed on base 54A of filter wheel 48 while mid-IR and/or other IR ranges transmitting filters can be disposed on sidewall 54B of the filter wheel.

Similar to filter wheel 18, filter wheel 48 is rotatably mounted to housing 12 via bearing structure 26. In this embodiment, bearing structure 26 can be sized to accommodate the wider sidewall 54B of filter wheel 48. For example, spindle 28 of bearing structure 26 can be made longer to accommodate the width of sidewall 54B of filter wheel 48. Similar to the embodiment depicted in FIG. 2, motor 19 is used to rotate filter wheel 48, as described in the above paragraphs.

Instead of providing one beam splitter 17 within filter wheel 18, a plurality of beam splitters 47A, 47B and 47C can be positioned within filter wheel 48. For example, beam splitter 47A can be positioned within filter wheel 48 so as to direct a portion of the radiation beam towards a filter wheel 52B in a third row of sidewall 54B. Beam splitter 47B can be positioned within filter wheel 48 so as to direct a portion of the radiation beam towards a filter wheel 52B in a second row of sidewall 54B. Beam splitter 47C can be positioned within filter wheel 48 so as to direct a portion of the radiation beam towards a filter wheel 52B in a first row of sidewall 54B. Similarly, instead of providing a radiation detector 21 disposed facing the sidewall of the filter wheel 48 as depicted in FIGS. 2 and 3, a plurality of radiation detectors 21A, 21B and 21C can be disposed facing each row of the sidewall 54B of the filter wheel 48. For example, the radiation detector 21C can be positioned facing the first row of the sidewall 54B closest to the base 54A, the radiation detector 21B can be positioned facing the second row (central row) of sidewall 54B, and radiation detector 21A can be positioned facing the third row of sidewall 54B, as depicted in FIG. 6.

In one embodiment, each of beam splitters 47A, 47B and 47C splits an incident radiation beam into two beams in two spectral regions without substantial energy loss. In another embodiment, each of beam splitters 47A, 47B and 47C splits an incident beam into two beam portions (e.g., having approximately equal intensity) without splitting the spectrum of the incident beam 100 into two spectral regions. In this instance, a conventional relatively non-expensive semi-reflecting or semi-transparent mirror at the radiation of interest can be used as a beam splitter 47A, 47B, 47C.

In operation, when filter wheel 48 is disposed in spectrometer 10 depicted in FIG. 1, in the same fashion as filter wheel 18, radiation beam 100 emitted by the radiation source 16 is directed towards the opening 12A of housing 12 to be transmitted through window 15A in opening 14A in airway adapter 14. Radiation beam 100 that passed through the window in opening 14A passes through a central portion 15 of airway adapter 14, then through window 15B in opening 14B to exit through opening 12B in housing 12.

Windows 15A and 15B in openings 14A and 14B are selected from a material so as to be substantially transparent at wavelengths of radiation of interest (e.g., between about 3 μm and about 15 μm) in the radiation emitted by the radiation source 16. A spectral portion of the beam 100 is absorbed by molecules (e.g., $CO_2$, $N_2O$, or other chemical substances, or any combination of two or more thereof) that are present in airway adapter 14. Radiation beam 100 exiting from opening 12B is split by beam splitter 47A disposed within filter wheel 48 into two radiation beams 100A and 100B. Radiation beam 100A is directed (for example, in a direction oriented out of the plane of FIG. 6) towards one of the filters 52B located in the third row in sidewall 54B of filter wheel 48 before reaching the detector 21A facing the third row in the sidewall 54B. Radiation beam 100B is directed towards splitter 47B disposed within filter wheel 48. Radiation beam 100B is split by beam splitter 47B into two radiation beams 100C and 100D. Radiation beam 100C is directed towards one of filters 52B located in the second row in sidewall 54B before reaching detector 21B facing the second row in sidewall 54B. Radiation beam 100D is directed towards beam splitter 47C disposed within filter wheel 48. Radiation beam 100D is split by beam splitter 47C into two radiation beams 100E and 100F. Radiation beam 100E is directed towards one of the filters 52B located in the first row in sidewall 54B before reaching detector 21C facing the third row in sidewall 54B. Radiation detector 100F passes through one of the filters 52A before reaching detector 20 facing base 54A of filter wheel 48.

Each filter 52A on base 54A of filter wheel 48 and each filter 52B in each row on sidewall 54B of the filter wheel can be selected to transmit a wavelength region of the spectrum specific to an absorption region of a compound. For example, two filters 52A on base 54A of filter wheel 48 can be selected to transmit a portion of the wavelength spectrum centered around a wavelength region of interest in the absorption spectrum of $CO_2$. Similarly, filter 52B can be selected to transmit a portion of the wavelength spectrum centered around a wavelength region of interest (for example a region in the absorption spectrum of a chemical agent such as halothane). By providing a plurality of sidewall filters 52B and detectors 21A, 21B and 21C associated with each row of filters 52B in sidewall 54B, absorption at a plurality of wavelength regions can be simultaneously measured. Furthermore, multiple rows (e.g., first and second rows) can be assigned to the same general spectral region so as to measure spectral details of the spectral region. Alternatively, multiple rows (e.g., first and second rows) can be assigned to identical spectral regions so as to provide better measurements results statistics.

In one embodiment, filter wheel 48 can be constructed such that base 54A of the filter wheel is rotatable while sidewall 54B of the filter wheel is fixed. Alternatively, filter wheel 48 can also be constructed such that sidewall 54B of filter wheel 48 is rotatable while base 54A of the filter wheel is fixed. In this way, base 54A or the sidewall 54B of filter wheel 48 can be independently rotated of the other if desired. In yet another embodiment, sidewall 54B and base 54A are both rotatable, but rotatable independently of one another. Such an arrangement provides added flexibility.

In one embodiment, the plurality of beam splitters 47A, 47B and 47C can be mounted to one or more movable mounts (not shown). The one or more movable mounts can be motorized or mechanically movable. The one or more movable mounts enables selected beam splitters 47A, 47B and/or 47C to be moved out of the path of the radiation beam 100. When beam splitters 47A, 47B and/or 47C are moved out of the path of radiation beam 100, radiation beam 100 will not be split into two beams by the beam splitters 47A, 47B and/or 47C. For example, when beam splitters 47A, 47B and 47C are moved out of the path of the radiation beam 100, the radiation beam 100 continues in its path along the X-X axis towards one of filters 52A disposed on base 54A of filter wheel 48 before reaching the radiation detector 20.

When selected beam splitters, for example beam splitters 47A and 47B, are moved out of the path of radiation beam 100 while beam splitter 47C is not moved out of the path of radiation beam 100, radiation beam 100 is split into two beams by beam splitter 47C. One portion of radiation beam 100 is directed towards one of filters 52B located in the first row in sidewall 54B before reaching detector 21C facing the third row in sidewall 54B and another portion of the radiation beam passes through one of the filters 52A located in base 54A before reaching detector 20 facing base 54A of filter wheel 48. As a result, the radiation beam can be directed and split as desired by positioning appropriate beam splitters in front of radiation beam 100.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

Although, the spectrometer and the filter wheel of the present invention are described herein as being usable for the purpose of measuring compounds or gases in a respiratory tract of a patient, it can be appreciated that the spectrometer and/or the filter wheel can be used in other medical applications such as for measuring chemicals (e.g., glucose) in the blood stream or used in other non-medical applications such as measuring fluid (e.g., liquid and/or gas) concentrations in an industrial setting or measuring fluids (e.g., gases) in environmental applications.

It should be appreciated that in one embodiment, the drawings herein are drawn to scale (e.g., in correct proportion). However, it should also be appreciated that other proportions of parts may be employed in other embodiments.

Furthermore, since numerous modifications and changes will readily occur to those of skill in the art, it is not desired to limit the invention to the exact construction and operation described herein. Accordingly, all suitable modifications and equivalents should be considered as falling within the spirit and scope of the invention.

What is claimed:

1. A spectrometer, comprising:
   (a) a filter wheel comprising:
      (1) a body comprising a base and a sidewall, the body configured to be rotatable about an axis of rotation,
      (2) a plurality of radiation filters disposed on the base; and
      (3) a plurality of radiation filters disposed on the sidewall, wherein the base and sidewall are integrally formed to define a one-piece body; and
   (b) a first radiation detector arranged to detect radiation received by the filters disposed on the base;
   (c) a second radiation detector arranged to detect radiation received by the filters disposed on the sidewall; and
   (d) at least one radiation beam splitter configured to split a beam of radiation into a first radiation beam portion and second radiation beam portion so that the first radiation beam portion is received by the first radiation detector and the second radiation beam portion is received by the second radiation detector.

2. The filter wheel of claim 1, wherein the sidewall and the base are independently rotatable around the axis of rotation.

3. A spectrometer, comprising:
   a radiation source capable of generating a radiation beam;
   a beam splitter that receives the radiation beam and splits the radiation beam into a first detection path and a second detection path;
   a filter wheel, the filter wheel having a first support structure on which a first plurality of filters are mounted and a second support structure on which at least one filter is provided, wherein the first plurality of filters are selectively movable into the first detection path, and wherein the at least one filter on the second support structure is arranged to be disposed in the second detection path;
   a first radiation detector arranged to detect radiation that passes through the selected filter in the first detection path; and
   a second radiation detector arranged to detect radiation that passes through the filter in the second detection path.

4. The spectrometer of claim 3, wherein the beam splitter is movable out of a path of the radiation beam.

5. The spectrometer of claim 3, wherein the first support structure and the second support structure are part of a same body so as to be movable together as one-piece.

6. The spectrometer of claim 3, wherein the first support structure comprises a base wall and the second support structure comprises a sidewall.

7. The spectrometer of claim 3, wherein the first support structure comprises a sidewall and the second support structure comprises a base wall.

8. The spectrometer of claim 3, wherein the first support structure and the second support structure are independently rotatable.

9. The spectrometer of claim 3, wherein the at least one filter provided on the second support structure is selected to transmit in an infrared spectrum region.

10. The spectrometer of claim 9, wherein the infrared spectrum region includes wavelengths between approximately 7 µm and approximately 15 µm.

11. The spectrometer of claim 3, wherein one or more of the first plurality of filters mounted on the first support structure are selected to transmit in a mid-infrared spectrum region.

12. The spectrometer of claim 11, wherein the mid-infrared spectrum region includes wavelengths between approximately 3 µm and approximately 8 µm.

13. The spectrometer of claim 11, wherein the mid-infrared region includes wavelengths between approximately 3.5 µm and approximately 5 µm.

14. The spectrometer of claim 3, wherein the first plurality of radiation filters disposed on the first support structure include a filter selected to transmit around an absorption band of $CO_2$, a filter selected to transmit around an absorption peak of $N_2O$, or a filter selected to transmit around an absorption band of a reference substance, or any combination of two or more thereof.

15. A spectrometer, comprising:
   a housing;
   a rotatable body disposed in the housing and having a base on which a first plurality of filters are disposed and a sidewall on which a second plurality of filters are disposed, the first plurality of filters and the second plurality of filters being structured to transmit desired wavelength ranges of radiation;
   a beam splitter that receives a radiation beam and splits the radiation beam into a first detection path and a second detection path;
   a first radiation detector arranged to detect radiation that passes through a filter of the first plurality of filters in the first detection path;
   a second radiation detector arranged to detect radiation that passes through a filter of the second plurality of filters in the second detection path;
   a spindle mounted to the body; and
   a plurality of seating cups mounted within the housing, wherein the spindle contacts the plurality of seating cups and is rotatably held by the plurality of seating cups, the spindle defining an axis of rotation of the rotatable body,
   wherein the spindle comprises a plurality of semi-spherical ends, and each of the plurality of seating cups comprises a concave surface.

16. The spectrometer of claim 15, wherein each of the plurality of semi-spherical ends is in contact with the concave surface of each of the plurality of seating cups.

17. The spectrometer of claim 15, wherein the body comprises a first support structure and a second support structure, the first support structure being configured to hold the first plurality of filters and the second support structure being configured to hold the second plurality of filters.

18. The spectrometer of claim 17, wherein the first support structure is mounted to the spindle.

19. The spectrometer of claim 17, wherein the first support structure and the second support structure are movable together as one-piece.

20. The spectrometer of claim 17, wherein the first support structure and the second support structure are independently rotatable.

21. The spectrometer of claim 17, wherein the first support structure comprises a base wall and the second support structure comprises a sidewall.

22. The spectrometer of claim 17, wherein the first support structure comprises a sidewall and the second support structure comprises a base wall.

23. The spectrometer of claim 17, wherein the first plurality of filters is azimuthally spaced apart such that two successive radiation filters are separated by the same angle around an axis of rotation of the body.

24. The spectrometer of claim 17, wherein the second plurality of filters is equidistantly spaced apart around the second support structure.

25. The spectrometer of claim 17, wherein the second plurality of filters is arranged in a staggered fashion.

26. The spectrometer of claim 15, wherein the rotatable body comprises an armature portion, the armature portion being mounted on a periphery of the body.

27. The spectrometer of claim 26, further comprising a motor configured to rotate the rotatable body, the motor comprising a rotor portion and a stator portion, the rotor portion being part of the armature portion.

28. The spectrometer of claim 26, wherein the stator portion is configured to interact with the rotor portion of the motor to rotate the body.

29. The spectrometer of claim 15, further comprising a radiation source capable of generating the radiation beam.

30. The spectrometer of claim 15, wherein the spindle comprises a plurality of semi-spherical ends, and each of the plurality of seating cups comprises a concave surface.

* * * * *